US006239220B1

(12) United States Patent
Sanghvi et al.

(10) Patent No.: US 6,239,220 B1
(45) Date of Patent: May 29, 2001

(54) RECOVERY OF TRIARYLMETHYL HALIDE PROTECTING GROUPS CLEAVED DURING OLIGONUCLEOTIDE SYNTHESIS

(75) Inventors: Yogesh S. Sanghvi, Encinitas; Zhiqiang Guo, San Diego, both of CA (US)

(73) Assignee: Isis Pharmaceuticals, Inc., Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 45 days.

(21) Appl. No.: 09/356,194

(22) Filed: Jul. 16, 1999

Related U.S. Application Data

(63) Continuation-in-part of application No. 09/118,614, filed on Jul. 17, 1998.

(51) Int. Cl.[7] ........................ C08F 214/02; C08F 114/02; C09B 11/04

(52) U.S. Cl. ........................ 525/115; 525/333.3; 552/101; 552/108; 552/115

(58) Field of Search ..................... 525/333.3, 333.4; 552/101, 108, 115

(56) References Cited

U.S. PATENT DOCUMENTS

| Re. 34,069 | 9/1992 | Köster et al. ..................... 536/27 |
|---|---|---|
| 3,687,808 | 8/1972 | Merigan et al. ..................... 195/28 |
| 4,415,732 | 11/1983 | Caruthers et al. ..................... 536/27 |
| 4,458,066 | 7/1984 | Caruthers et al. ..................... 536/27 |
| 4,500,707 | 2/1985 | Caruthers et al. ..................... 536/27 |
| 4,668,777 | 5/1987 | Caruthers et al. ..................... 536/27 |
| 4,725,677 | 2/1988 | Köster et al. ..................... 536/27 |
| 4,973,679 | 11/1990 | Caruthers et al. ..................... 536/27 |
| 5,132,418 | 7/1992 | Caruthers et al. ..................... 536/27 |
| 5,563,220 | * 10/1996 | Webber et al. ..................... 525/333.3 |
| 5,922,890 | * 7/1999 | Bleicher ..................... 552/115 X |

FOREIGN PATENT DOCUMENTS

| 43 06 839 A1 | 9/1994 | (DE) . |
| WO 98/39290 | 9/1998 | (WO) . |

OTHER PUBLICATIONS

Sabirov, A.N. et al. In Peptides: Chemistry, Structure and Biology. P.T.P. Kaumaya, R.S. Hodges, Eds. Mayflower Scientific, Ltd.: England, 1996; pp. 117–118.*
Harre, M. et al. "An efficient method for activation and recycling of trityl resins." Reactive & Functional Polymers vol. 41(1999), pp. 111–114.*

Bleasdale, C. et al., "4,4'–Dimethoxytrityl and 4–Monomethoxytrityl Tetrafluoroborate: Convenient Reagents for the Protection of Primary Alcohols Including Sugars", *J. Chem. Soc. Perkin Trans.*, 1990, 1, 803–805.

Brill, W., "Facile Methods to Recycle Nucleosides during Solid Phase Synthesis of Oligonucleotides", *Tetrahedron Letts.*, 1994, 35(19), 3041–3044.

Cook, P.D., "Medicinal chemistry of antisense oligonucleotides—future opportunities", *Anti–Cancer Drug Design*, 1991, 6, 585–607.

Delgado, C. et al., "The Uses and Properties of PEG–Linked Proteins", *Crit. Rev. in Therapeutic Drug Carrier Sys.*, 1992, 9, 249–304.

Ding et al., "Detritylation of mono– and di–saccharide derivatives using ferric chloride hydrate", *Carbohydrate Res.*, 1997, 303, 445–448.

Engels, "Selective Electrochemical Removal of Protecting Groups in Nucleotide Synthesis", *Angew. Chem. Int. Ed. Engl.*, 1979, 18(2), 148–149.

Englisch, U. et al., "Chemically Modified Oligonucleotides as Probes and Inhibitors", *Angew. Chem. Int. Ed. Eng.*, 1991, 30, 613–629.

Greene et al., "Use of the Naphthalene Radical Ion in Deblocking O–Methoxytrityl Nucleotide Derivatives", *Tetrahedron Lett.*, 1975, 25, 2081–2084.

Guo, Z. et al., "Process for the Capture and Reuse of the 4,4'–Dimethoxytriphenylmethyl Group during Manufacturing of Oligonucleotides," *Org. Proc. Res. & Develop.*, 1998, 2, 415–417.

Kohli et al., "The Triphenylmethyl (Trityl) Group and its Uses in Nucleotide Chemistry", *Tetrahedron Lett.*, 1980, 21, 2683–2686.

Kroschwitz, J.I., "Polynucleotides", *Concise Encyclopedia of Polymer Science and Engineering*, 1990, John Wiley & Sons, New York, 858–859.

Letsinger et al., "Selective Deprotection by Reductive Cleavage with Radical Anions", *J. Am. Chem. Soc.*, 1975, 97(24), 7197–7198.

Matteucci et al., "The Use of Zinc Bromide for Removal of Dimethoxytrityl Ethers from Deoxynucleosides", *Tetrahedron Lett.*, 1980, 21, 3243–3246.

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

(List continued on next page.)

Primary Examiner—Michael G. Ambrose
(74) Attorney, Agent, or Firm—Woodcock Washburn Kurtz Mackiewicz & Norris LLP (57) ABSTRACT

The present invent n provides a method for the preparation of triarylmethyl protecting group reagents. The reagents are prepared from reaction effluent from the cleavage step of oligonucleotide synthetic regimes.

19 Claims, 2 Drawing Sheets

OTHER PUBLICATIONS

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333.

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 273–288.

Sanghvi et al., "Carbohydrates: Synthetic Methods and Applications in Antisense Therapeutics", in Carbohydrate Modifications in Antisense Research, ACS Symposium Series 580, ACS Publications, Washington, DC, 1994, Ch. 1, 1–22.

Scremin et al., "Stepwise Regeneration and Recovery of Deoxyribonucleoside Phosphoramidite Monomers during Solid–Phase Oligonucleotide Synthesis", *J. Org. Chem.*, 1994, 59, 1963–1966.

Yang et al., "Facile Selective Detritylation of 5'–Primary Alcohols of Pyrimidine Nucleosides Using Tetra–n–butylammonium Peroxydisulfate", *Heteroatom Chem.*, 1997, 8(5), 435–438.

Alul, R.H. et al., "Oxalyl–CPG: a labile support for synthesis of sensitive oligonucleotide derivatives", *Nucl. Acid Res.*, 1991, 19, 1527–1532.

Bunin, B.A., "Linkers for Solid–Phase Synthesis," in *The Combinatorial Index*, Academic Press, 1998, 52–55.

Hayatsu et al., "Studies on Polynucleotides. LXXII. Deoxyribooligonucleotide Synthesis on a Polymer Support," *J. Am. Chem. Soc.*, 1967, 89(15), 3880–3887.

Iyer et al., "Oligonucleotide Synthesis," in *Comprehensive Natural Products Chemistry*, Kool, E.T. (ed.), Elsevier, 1999, vol. 7, 105–152.

Rathore et al., "A new method for synthesis of 4, 4'–dimethoxytrityl chloride," *Indian J. Chem.*, 1995, 34B, 634–635.

Reese, C.B. et al., "The H–phosphonate approach to the synthesis of oligonucleotides and their phosphorothioate analogues in solution," Perkin, *J. Chem. Soc. Perkin Trans.*, 1999, 1, 1477–1486.

Wang, S.S., "Solid Phase Synthesis of Protected Peptides via Photolytic Cleavage of the α–Methylphenacyl Ester Anchoring Linkage," *J. Org. Chem.*, 1976, 41(20), 3258–3261.

Wright, P. et al., "Large Scale Synthesis of Oligonucleotides via phosphoramidite Nucleosides and a High–loaded Polystyrene Support", *Tetrahedron Letts.*, 1993, 34, 3373–3376.

* cited by examiner

Figure 1

Solid Phase Oligonucleotide Synthesis

Repeat i-v as necessary to obtain
desired oligomer linked to solid support effluent containing
orange-red DMT
cation:

in $CH_2Cl_2$
and excess $Cl_2CHCO_2H$

|   | R | R' |
|---|---|---|
| 1 | DMT | L/SS |
| 2 | H | L/SS |
| 3 | DMT | 5'-Protected-3'-nucleoside phosphoramidite |
| 4 | DMT | Activated 3'-nucleoside phosphoramidite |
| 5 | DMT | Phosphite triester ($P^{III}$) |
| 6* | Ac | L/SS or growing chain connected to L/SS |
| 7 | DMT | Phosphorothioate/ Phosphodiester; etc. ($P^V$) |

* represents structure of capped, uncoupled shortmer i = 3% $Cl_2CHCO_2H$ in $CH_2Cl_2$;
ii = $CH_3CN$ wash;
iii = 0.2 M solution of 3 / 0.45 M 1-$H$ tetrazole in $CH_3CN$;
iv = Oxidation
v = Capping reagents.
DMT = 4,4'-dimethoxy triphenylmethyl chloride;
L/SS: linker-solid-support;
B: T, $C^{Bz}$, $A^{Bz}$, or $G^{iBu}$

Figure 2

Preparation of DMT Amidite Reagent

Effluent from deprotection step containing orange-red DMT cation:

in $CH_2Cl_2$
and excess $Cl_2CHCO_2H$ a → b → c → d → e → f → DMT-Cl a = Concentration to an oil under reduced pressure
b = MeOH; 3N NaOH
c = extraction of DMT-OH with organic solvent
d = add AcCl in toluene; hold at reflux for 3 hours
e = Concentration to an oil under reduced pressure
f = recrystallization (e.g., cyclohexane)

RECOVERY OF TRIARYLMETHYL HALIDE PROTECTING GROUPS CLEAVED DURING OLIGONUCLEOTIDE SYNTHESIS

CROSS REFERENCE TO RELATED APPLICATIONS

This application is a continuation in part of U.S. applications Ser. No. 09/118,614 filed Jul. 17, 1998 the content of which is incorporated by reference herein in its entirety.

FIELD OF THE INVENTION

The present invention is directed to methods for preparing triarylmethyl protecting group reagents. In preferred embodiments, the present invention provides methods for preparing protecting group reagents from products of oligonucleotide synthesis, preferably from waste products generated during cleavage of protecting groups during oligonucleotide synthesis.

BACKGROUND OF THE INVENTION

Modern therapeutic efforts are generally focused on the functions of proteins which contribute to many diseases in animals and man. There have been numerous attempts to modulate the production of such proteins by interfering with the function of biomolecules, such as intracellular RNA, that are involved in the synthesis of these proteins. It is anticipated that protein production will thus be inhibited or abolished, resulting in a beneficial therapeutic effect. The general object of such therapeutic approaches is to interfere with or modulate gene expression events that lead to the formation of undesired proteins.

One such method for the inhibition of specific gene expression is the use of oligonucleotides and oligonucleotide analogs as "antisense" drugs. These oligonucleotide or oligonucleotide analogs are designed to be complementary to a specific, target, messenger RNA (mRNA) or DNA, that encodes for the undesired protein. The oligonucleotide or oligonucleotide analog is expected to hybridize with good affinity and selectivity to its target nucleic acid, such that the normal essential functions of the target nucleic acid are disrupted. Antisense therapeutics hold great promise, as evidenced by the large number of oligonucleotides and oligonucleotide analogs that have been evaluated clinically in recent times. See generally, Ciba Foundation Symposium 209, *Oligonucleotides as Therapeutic Agents*, John Wiley & Sons, 1997. Further, oligonucleotides and oligonucleotide analogs have shown significant promise in the diagnosis of disease, and have also been used extensively as probes in diagnostic kits and as research reagents.

Figure 1:
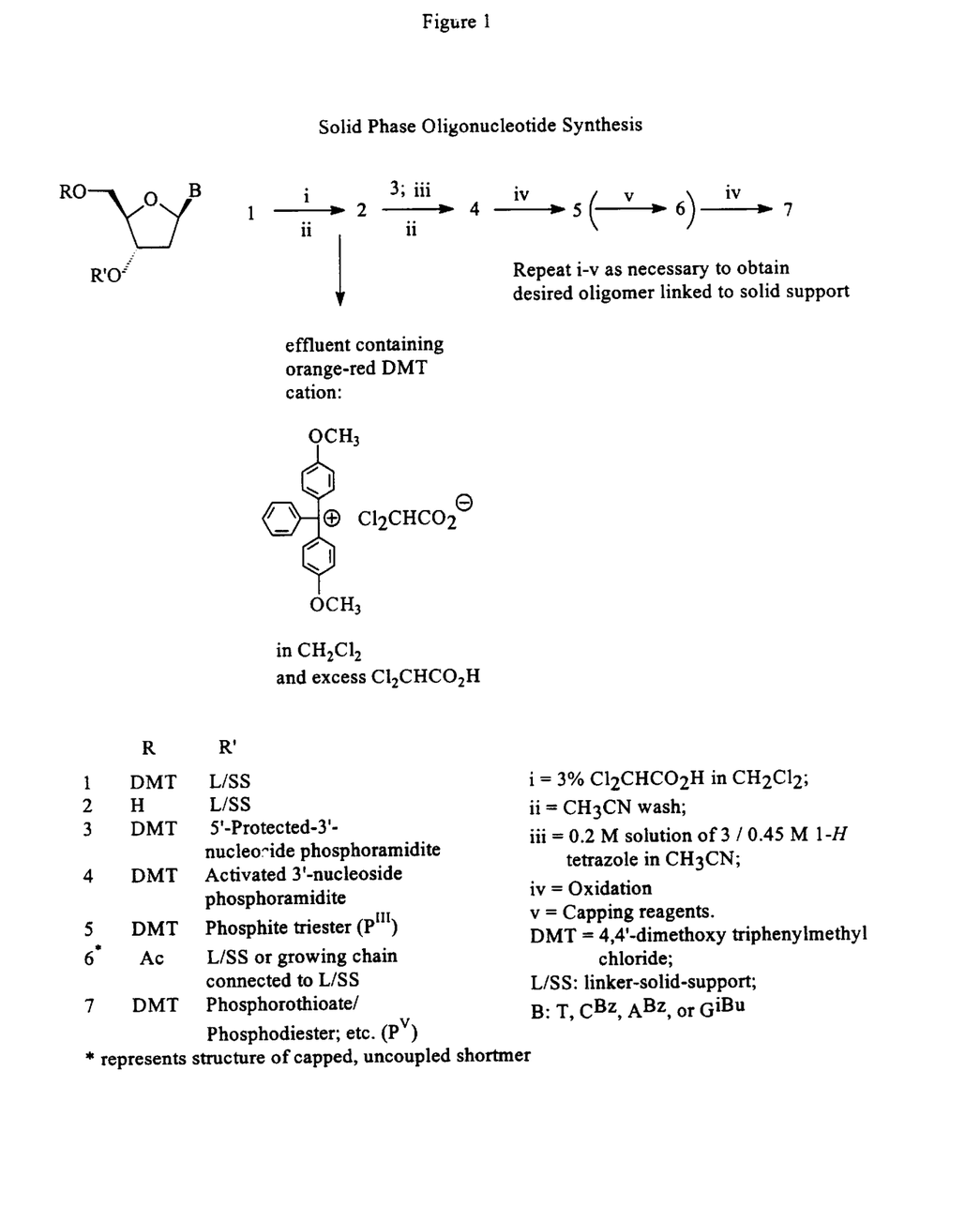
FIG. 1 shows a typical solid state oligonucleotide synthetic protocol.

There is therefore a great need for the large scale production of oligonucleotides and oligonucleotide analogs for commercial application. The predominant synthetic regime currently in use for oligonucleotide synthesis is the phosphoramidite method, which is summarized in FIG. 1. Briefly, oligonucleotides are synthesized on a solid-support via sequential reactions (shown as I-v in FIG. 1) in a predetermined order, typically controlled by a computerized pumping system. For example, synthesis typically begins with a nucleoside linked to a solid-support, typically via a linker molecule attached to the 3'-oxygen of the first nucleosidic synthon (as shown in FIG. 1, compound 1). Deprotection (or "cleavage") of the 5'-hydroxyl group is effected by treatment with deprotecting ("deblocking") solution I, 3% dichloroacetic acid (DCA) in dichloromethane, which removes the 5'-O-(4,4'-dimethoxytriphenylmethyl) hydroxyl protecting group to provide 2, having a free 5'-OH group. Such protecting groups are routinely used in oligonucleotide synthesis to allow selective reaction between two functional groups while protecting all other functionalities present in the reacting molecules.

Deprotection of the nucleoside 5'-O-DMT group as described above causes the release of a DMT cation (shown in FIG. 1), which has a characteristic bright red-orange color. Appearance of the colorful DMT cation facilitates monitoring of the coupling efficiency, and also is used by the computer system as a signal to discontinue the flow of 3% DCA deblocking solution.

Deprotection of triarylmethyl protecting groups such as DMT groups under acidic conditions is reported to be a reversible reaction. Therefore, removal of all of the DMT cation from the solid-support is crucial for the success of the deblocking step. Accordingly, in step ii the support is washed with dry solvent, typically acetonitrile (ACN), which removes traces of acidic solution and any trapped DMT-cation.

In step iii, a nucleoside phosphoramidite (3) is premixed with 1-H tetrazole to produce a very reactive P(III) tetrazolide intermediate (4) that reacts almost immediately with the 5'-OH group of (2) generating (5), which has a phosphite triester internucleosidic linkage. The unreacted excess (4) is then washed from the support with dry ACN.

The unstable P(III) species of (5) is then oxidized to a more stable P(V) internucleosidic linkage, such as a phosphodiester or phosphorothioate, to furnish a dimer or higher order support bound species, such as 7. A capping reaction (represented in FIG. 1 as Step v) is then performed to prevent unreacted 5'-OH groups from further extension. Typically, capping is performed with an acylating reagent. These steps are then repeated iteratively until the desired oligonucleotide is obtained. A more detailed treatment of oligonucleotide synthesis, and further representative synthetic procedures can be found in *Oligonucleotides And Analogues A Practical Approach*, Ekstein, F. Ed., IRL Press, New York, 1991, which incorporated herein in its entirety.

The preceding synthetic regime creates two large molecular weight waste products—one half mole excess of building block 4 (discarded in the process in ACN with 1-H tetrazole as an activator) and the triarylmethyl protecting group used for 5'-OH protection. The latter amounts to approximately 35% weight of the incoming monomeric phosphoramidite unit 3, and is released as triarylmethyl protecting group cation, typically in dichloromethane. Such triarylmethyl protecting groups are usually tailored molecules with distinct reactivity and stability to specific reaction conditions. Thus, they are expensive and add significantly to the cost of the synthetic process.

One critical challenge in the commercialization of oligonucleotide based therapeutic and diagnostic products is the ability to manufacture and market these products at a reasonable cost with minimal environmental impact. One solution to these problems is to minimize the waste of the nucleoside phosphoramidites used in the chemical syntheses. Thus, attempts have been made to recycle the excess unreacted amidite during synthesis of oligonucleotides. See for example Brill W., *Tetrahedron Letts.*, 1994, 35, 3041; Scremin et al., *J. Org. Chem.*, 1994, 59, 1963. However, these techniques have not been reported to have been successfully applied to the large-scale manufacture of oligonucleotides, as is required for research or commercial purposes.

It can be seen that there exists a need for synthetic methods that address the shortcomings of oligonucleotide synthesis discussed above. To date, there has been no report of the capture and use of protecting group cations generated during the deprotection of protected hydroxyl groups in oligonucleotide synthesis. The present invention is directed to this, as well as other, important ends.

SUMMARY OF THE INVENTION

The present invention provides novel methods for the preparation of triarylmethyl protecting group reagents. In preferred embodiments, the triarylmethyl protecting group reagents are prepared from a by-product of standard oligonucleotide synthetic reactions.

In some preferred embodiments, synthetic methods are provided comprising:
  providing a monomeric or oligomeric nucleobase bearing compound having a hydroxyl group, the hydroxyl group being protected with a triarylmethyl protecting group;
  treating the compound with a deprotecting reagent to produce a free triarylmethyl protecting group;
  contacting the free triarylmethyl protecting group with a base to form a triarylmethyl alcohol; and
  reacting the triarylmethyl alcohol with a halide reagent to form a triarylmethyl halide protecting reagent.

In some preferred embodiments, the triarylmethyl halide protecting reagent has the Formula:

wherein:
  $X_1$ is Cl, Br or I; and
  each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, and pyrenyl; or $Ar_1$ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, or pyrenyl; or $Ar_2$ and $Ar_3$ together form xanthanen-9-yl or thioxanthen-9-yl.

In more preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4', 4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred.

Preferably, the base is sodium hydroxide, potassium hydroxide, lithium hydroxide or barium hydroxide, with sodium hydroxide being more preferred.

In some preferred embodiments, the halide reagent is acetyl chloride, acetyl bromide, acetyl iodide, thionyl chloride, thionyl bromide, phosphorus trichloride, phosphorus tribromide, phosphorus oxychloride, or carbon tetrabromide, with acetyl chloride being more preferred.

In further preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4', 4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred; the base is sodium hydroxide, potassium hydroxide, lithium hydroxide or barium hydroxide, with sodium hydroxide being more preferred; and the halide reagent is acetyl chloride, acetyl bromide, acetyl iodide, thionyl chloride, thionyl bromide, phosphorus trichloride, phosphorus tribromide, phosphorus oxychloride, or carbon tetrabromide, with acetyl chloride being more preferred.

In further preferred embodiments, the contacting of the free triarylmethyl protecting group with the base is performed in a water-miscible organic solvent, which is preferably methanol, ethanol, propanol, acetonitrile, or tetrahydrofuran, with methanol being more preferred.

In still further preferred embodiments, the triarylmethyl alcohol is reacted with the halide reagent in a water-immiscible solvent, which is preferably diethyl ether, dasopropyl ether, ethyl acetate, dichloromethane, chloroform, or toluene, with toluene being more preferred.

The present invention also provides synthetic methods comprising:
  providing a monomeric or oligomeric nucleobase bearing compound having a hydroxyl group, the hydroxyl group being protected with a triarylmethyl protecting group;
  treating the compound with a deprotecting reagent to produce a free triarylmethyl protecting group;
  contacting the free triarylmethyl protecting group with a base to form a triarylmethyl alcohol; and
  reacting the triarylmethyl alcohol with a tetrahaloborate reagent to form a triarylmethyl teterahaloborate protecting reagent.

Preferably, the triarylmethyl teterahaloborate protecting reagent has the Formula:

wherein:

$X_2$ is a tetrahaloborate; and each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, and pyrenyl; or $Ar_1$ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, or pyrenyl; or $Ar_2$ and $Ar_3$ together form xanthanen-9-yl or thioxanthen-9-yl.

More preferably, the tetrahaloborate is trityl, monomethoxytrityl (MMTr), 4,4'-dimethoxytrityl (DMTr), 4,4',4"-trimethoxytrityl (TMTr), 4,4', 4"-tris-(benzoyloxy) trityl (TBTr), 4,4',4"-tris(4,5-dichlorophthalimido)trityl (CPTr), 4,4', 4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred.

In some preferred embodiments, the base is sodium hydroxide, potassium hydroxide, lithium hydroxide or barium hydroxide, with sodium hydroxide being preferred.

In some preferred embodiments, the tetrahaloborate reagent is tetrafluoroboric acid in acetic anhydride.

In more preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred; the base is sodium hydroxide, potassium hydroxide, lithium hydroxide or barium hydroxide, with sodium hydroxide being more preferred; and the tetrahaloborate reagent is tetrafluoroboric acid in acetic anhydride.

Also provided in accordance with the present invention are methods for the preparation of a triarylmethyl halide or tetrahaloborate protecting reagent having the Formula:

wherein:

$X_3$ is Cl, Br, I, or tetrahaloboronyl; and each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, and pyrenyl; or $Ar_1$ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, or pyrenyl; or $Ar_2$ and $Ar_3$ together form xanthanen-9-yl or thioxanthen-9-yl;

comprising the steps of:

cleaving a triarylmethyl protecting group during the course of oligonucleotide synthesis;

collecting the effluent from the cleavage, the effluent containing free triarylmethyl protecting group;

contacting the free triarylmethyl protecting group with a base to form a triarylmethyl alcohol; and reacting the triarylmethyl alcohol with a) a halide reagent to form the triarylmethyl halide protecting reagent; or b) a tetrahaloborate reagent to form the triarylmethyl teterahaloborate protecting reagent.

In some preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being preferred.

In further preferred embodiments, the base is sodium hydroxide, potassium hydroxide, lithium hydroxide or barium hydroxide, with sodium hydroxide being preferred.

In more preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris-(levulinyloxy)trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl with 4,4'-dimethoxytrityl being more preferred; the base is sodium hydroxide, potassium hydroxide, lithium hydroxide or barium hydroxide, with sodium hydroxide being more preferred; and the tetrahaloborate reagent is tetrafluoroboric acid in acetic anhydride.

In some preferred embodiments, the contacting of the free triarylmethyl protecting group with the base is performed in a water-miscible organic solvent, which is preferably methanol, ethanol, propanol, acetonitrile, or tetrahydrofuran, with methanol being more preferred.

In some especially preferred embodiments of the foregoing methods, the triarylmethyl protecting group is 4,4'-dimethoxytrityl, the base is sodium hydroxide, and the halide reagent is acetyl chloride.

In further preferred embodiments, synthetic methods are provided comprising:
  providing a compound having an alcohol, amine, caboxylic acid, phenol, imidazole or thiol functionality, the alcohol, amine, caboxylic acid, phenol, imidazole or thiol functionality being protected with a solid support bound triarylmethyl protecting group;
  treating the compound with a deprotecting reagent to produce a solid support bound triarylmethyl cation;
  contacting the solid support bound triarylmethyl cation with a base to form a solid support bound triarylmethyl alcohol; and
  reacting the solid support bound triarylmethyl alcohol with a halide reagent to form a triarylmethyl halide protecting reagent.

In some preferred embodiments, the triarylmethyl halide protecting reagent has the Formula:

wherein:
  X is Cl, Br or I;
  SS is a solid support which can include an optional linking moiety; and
  each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, and pyrenyl; or $Ar_1$ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3, 5-hexadienoxy)-phenyl, 4-(4,5-dichlorophthalimido) phenyl, napthyl, anthracenyl, or pyrenyl; or $Ar_2$ and $Ar_3$ together form xanthanen-9-yl or thioxanthen-9-yl.

In more preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris-(levulinyloxy)trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred.

Preferably, the base is sodium hydroxide, potassium hydroxide, lithium hydroxide or barium hydroxide, with sodium hydroxide being more preferred.

In some preferred embodiments, the halide reagent is acetyl chloride, acetyl bromide, acetyl iodide, thionyl chloride, thionyl bromide, phosphorus trichloride, phosphorus tribromide, phosphorus oxychloride, or carbon tetrabromide with acetyl chloride being more preferred.

In further preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris(levulinyloxy)trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)-methyl (TTTr), or 4,4'-di-3,5-hexadienoxytrityl with 4,4'-dimethoxytrityl being more preferred; the base is sodium hydroxide, potassium hydroxide, lithium hydroxide or barium hydroxide with sodium hydroxide being more preferred; and the halide reagent is acetyl chloride, acetyl bromide, acetyl iodide, thionyl chloride, thionyl bromide, phosphorus trichloride, phosphorus tribromide, phosphorus oxychloride, or carbon tetrabromide with acetyl chloride being more preferred.

In further preferred embodiments, the contacting of the solid support bound triarylmethyl cation with a base is performed in a water-miscible organic solvent which is preferably methanol, ethanol, propanol, acetonitrile, or tetrahydrofuran.

In still further preferred embodiments, the solid support bound triarylmethyl alcohol is contacted with the halide reagent in a water-immiscible solvent, which is preferably diethyl ether, diisopropyl ether, ethyl acetate, dichloromethane, chloroform, or toluene.

In some preferred embodiments, the solid support is controlled pore glass, oxalyl-controlled pore glass, aminopolyethyleneglycol (TENTAGEL), polystyrene or a derivatized polystyrene with copoly(styrene 1% divinylbenzene) being more preferred.

DETAILED DESCRIPTION OF THE PREFERRED EMBODIMENTS

The present invention presents novel methods for preparing triarylmethyl protecting group reagents, preferably from by-products of oligonucleotide synthesis reactions.

The present invention also relates to the field of recovery and reuse of triarylmethyl halide resins and more particularly, to the regeneration of triarylmethyl halide groups that are attached to insoluble polymers. Such triarylmethyl halides attached to insoluble polymers are useful for solid-phase organic synthesis and combinatorial methodologies.

In some preferred embodiments, the methods of the invention comprise:

providing a monomeric or oligomeric nucleobase bearing compound having a hydroxyl group, the hydroxyl group being protected with a triarylmethyl protecting group;

treating the compound with a deprotecting reagent to produce a free triarylmethyl protecting group;

contacting the free triarylmethyl protecting group with a base to form a triarylmethyl alcohol; and reacting the triarylmethyl alcohol with a halide reagent to form a triarylmethyl halide protecting reagent.

In some preferred embodiments, the triarylmethyl halide protecting reagent has the Formula:

wherein:

$X_1$ is Cl, Br or I; and each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, and pyrenyl; or $Ar_1$ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3, 5-hexadienoxy)-phenyl, 4-(4,5-dichlorophthalimido) phenyl, napthyl, anthracenyl, or pyrenyl; or $Ar_2$ and $Ar_3$ together form xanthanen-9-yl or thioxanthen-9-yl.

More preferred $Ar_1$, $Ar_2$, and $Ar_3$ groups include trityl, monomethoxytrityl (MMTr), 4,4'-dimethoxytrityl (DMTr), 4,4',4''-trimethoxytrityl (TMTr), 4,4',4''-tris-(benzoyloxy) trityl (TBTr), 4,4',4''-tris(4,5-dichlorophthalimido)trityl (CPTr), 4,4',4''-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4''-tris-(tert-butylphenyl)methyl (TTTr), or 4,4'-di-3,5-hexadienoxytrityl, with 4,4'-dimethoxytrityl being more preferred.

Although the foregoing represents preferred embodiments of the methods of the invention, it will be appreciated that a large number of diverse members of this class of protecting groups are available and have been widely used in the art. Variations in the structure of trityl protecting groups have been designed to optimize or provide ease of protection and cleavage reactions, and alteration of the physicochemical properties of the monomers and oligonucleotides. The methods of the present invention find applicability in the preparation of such protecting groups.

The present invention affords significant advantages in the performance of oligonucleotide synthesis. For example, in accordance with the methods of the invention, the amount of waste generated at the deprotecting stage of oligonucleotide synthesis can be significantly reduced. Thus, the methods of the invention also provide oligonucleotide synthesis at reduced cost, and with a significantly lower ecological burden.

The current method of choice for the preparation of naturally occurring oligonucleotides, as well as modified oligonucleotides such as phosphorothioate oligonucleotides, is via solid-phase synthesis wherein an oligonucleotide is prepared on a polymer support (a solid support) such as controlled pore glass (CPG); oxalyl-controlled pore glass (see, e.g., Alul, et al., *Nucleic Acids Research* 1991, 19, 1527); TENTAGEL Support-aminopolyethyleneglycol derivatized polystyrene, (see, e.g., Wright, et al., *Tetrahedron Letters* 1993, 34, 3373); or POROS, a polystyrene resin available from Perceptive Biosystems. A number of resins which are amenable to the present invention and that are routinely used in solid phase organic synthesis are listed in the Calbiochem-Novabiochem Corp. Catalog for Combinatorial Chemistry 1999. Included in these resins are brominated [4-propionylphenoxy]-acetic acid resin; brominated Wang resin (Wang, S. S., *J. Org. Chem.*, 1976, 41, 3258); bromo-(4-methoxyphenyl)methyl polystyrene resin; 4-(bromomethyl)-pyenoxyethyl polystyrene resin; 4-bromo polystyrene resin; Merrifield resin (M. Bodansky, et al, in "Peptide Synthesis", E. Gross & J, Meinhofer [Eds], Academic Press, Y. Wiley, New York, 1976); and Merrifield 2% divinylbenzene resin. The present invention includes methods of preparing dimers and oligomers using monomers and oligomers that are attached to a solid support via a triarylmethyl protecting group that is preferably attached to a 5'-hydroxyl position of the synthon. Equipment for such synthesis is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), *Oligonucleotides and Analogues, a Practical Approach*, Oxford University Press, New York (1991).

Solid-phase synthesis relies on sequential addition of nucleotides to one end of a growing oligonucleotide chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. No. 4,725,677 and U.S. Pat. Re. 34,069.

The methods of the present invention are useful for the preparation of a wide variety of protecting group reagents that are in turn useful for the protection of hydroxyl groups, and in particular 5'-hydroxy groups of nucleoside building blocks used in oligonucleotide synthesis. In accordance with the preferred embodiments of the methods of the invention, a monomeric or oligomeric nucleobase bearing compound having a hydroxyl group protected with a triarylmethyl protecting group is treated with a deprotecting reagent to produce a free triarylmethyl protecting group. In preferred embodiments, the monomeric or oligomeric nucleobase bearing compound is the growing nucleotide chain in standard oligonucleotide synthesis, which is optionally attached to a solid support. As used herein, the term "treating the compound with a deprotection reagent" means bringing the compound and the deprotecting reagent into sufficient proximity such that the deprotection reaction occurs.

Depending on the nature of the purification strategy to be used, the 5'-protecting group on the terminal nucleoside unit of the oligonucleotide can be cleaved during the synthesis process (e.g., when ion-exchange purification may be desired) or cleaved post-synthesis (e.g., after reverse-phase purification of the oligonucleotide).

Deprotecting reagents useful in the methods of the invention include those known to be effective for removal of 5'-hydroxyl protecting groups. In some preferred methods of the present invention, cleavage is preferably performed under acidic conditions using a protic or Lewis acid in an organic solvent. Suitable organic solvents include dichloromethane, chloroform, carbon tetrachloride, toluene, xylene, acetonitrile and tetrahydrofuran. In addition to acidic deprotection protocols, deprotection protocols which avoid acidic conditions are also amenable to the present invention. Such protocols are advantageous in that they ameliorate the problems of depurination in purine rich oligonucleotides, occasionally seen with acidic deprotection. For example, the use of naphthalene radical anions in HMPT to effect cleavage of 5'-O-MMTr groups has been reported and used for solution phase oligonucleotide synthesis. See Greene and Letsinger, Tetrahedron Lett., 1975, 2081; Letsinger and Finnan, *J. Am. Chem. Soc.*, 1975, 97, 7197. Boron trifluoride etherate in dichloromethane also has been reported as useful for the cleavage of 5'-O-trityl protecting groups. See Engels, *Angew. Chem. Int. Ed. Engl.*, 1979, 18, 148. A milder Lewis acid such as zinc bromide in nitromethane or dichloromethane also has been used to cleave triarylmethyl protecting groups during solid phase oligonucleotide synthesis. See Matteucci and Caruthers, *Tetrahedron Lett.*, 1980, 21, 3243; Kohli et al., *Tetrahedron Lett.*, 1980, 21, 2683. Tetra-n-butyl ammonium peroxydisulfate has been found to be a good deprotecting reagent for the removal of trityl protecting groups. Cleavage of 5'-O-DMTr groups from nucleosides has been reported in excellent yields, under neutral and mild conditions without concomitant cleavage of the glycosidic bond. See Yang et al., *Heteroatom Chem.*, 1997, 8, 435. Quantitative cleavage of trityl ethers may also be accomplished using ferric chloride hexahydrate in dichloromethane, at room temperature, without affecting other protecting groups that may be present in the molecule. See Ding et al., *Carbohydrate Res.*, 1997, 303, 445. Other representative protecting groups and deprotecting reagents can be found, for example, in Greene and Wuts, *Protective Groups in Organic Synthesis*, 2d ed., John Wiley & Sons, New York, 1991, which is incorporated by reference in its entirety, and in Ekstein, supra. Each of the foregoing cleavage protocols, as well as others, are amenable to the methods of the invention.

In some preferred embodiments of the methods of the invention, each time a 5' protecting group is cleaved during oligonucleotide synthesis, the reaction effluent containing the protecting group cation product of the cleavage step is collected. The collection procedure can be modified, if desired, to allow for particular aspects of the synthesis, for example where some of the nucleobase synthons bear 5'-protecting groups that are different from those used for the construction of the remainder of the oligonucleotide.

In some preferred embodiments of the present invention, the organic solvent contained in the effluent is evaporated to yield a residue of the triarylmethyl cation.

In some preferred embodiments, this residue is dissolved in a water-miscible organic solvent, which is preferably methanol, ethanol, propanol, acetonitrile or tetrahydrofuran, with methanol being more preferable.

The solution of the triarylmethyl cations is subsequently contacted with excess base to form the alcohol of the triarylmethyl protecting group. Contacting of the triarylmethyl cation and base can be accomplished, for example, by adding a base solution to a solution of the cation. Representative bases useful for this purpose include aqueous sodium hydroxide, potassium hydroxide, lithium hydroxide or barium hydroxide, with 3 N sodium hydroxide being more preferable.

In some preferred embodiments of the present invention, the alcohol of the protecting group is extracted with a water-immiscible solvent to form a solution. Suitable water-immiscible solvents include, for example, diethyl ether, diisopropyl ether, ethyl acetate, dichloromethane, chloroform, and toluene, with toluene being more preferable.

According to the some preferred embodiments of the methods of the present invention, the solution containing the alcohol is reacted with a halide reagent to form the triarylmethyl protecting group reagent. Preferably, the halide reagent is in excess. As used herein, the term "reacting the triarylmethyl alcohol with a halide reagent" means placing the triarylmethyl alcohol together with the halide reagent for a time and under conditions of temperature and pressure such that the triarylmethyl protecting group reagent is formed. In some preferred embodiments, the alcohol is heated together with the halide reagent. Preferably, the alcohol is placed together with the halide reagent and held at reflux, for a period of time sufficient to form the triarylmethyl protecting group reagent, typically for about 1 to about 3 hours. Suitable halide reagents include, for example, acetyl chloride, acetyl bromide, acetyl iodide, thionyl chloride, thionyl bromide, phosphorus trichloride, phosphorus tribromide, phosphorus oxychloride, and carbon tetrabromide.

In some preferred embodiments, the water-immiscible solvent is evaporated to form a residue of triarylmethyl protecting group reagent, which can then be purified by any of a variety of standard purification techniques to afford the purified product. In some preferred embodiments, the purification is achieved by recrystalization from a suitable recrystalization solvent, for example pentane, hexane, cyclopentane, cyclohexane, cycloheptane, or toluene.

In some preferred embodiments, the triarylmethyl alcohol is reacted with a tetrahaloborate reagent to form a triarylmethyl teterahaloborate protecting reagent. In particularly preferred embodiments, the tetrahaloborate reagent is tetrafluoroborate, preferably in acetic anhydride. In preferred embodiments, the triarylmethyl teterahaloborate protecting reagent has the Formula:

wherein:
$X_2$ is a tetrahaloborate; and $Ar_1$, $Ar_2$, and $Ar_3$ are as described above.

Also provided in accordance with the present invention are methods for the preparation of a triarylmethyl halide or tetrahaloborate protecting reagent having the Formula:

wherein:
$X_3$ is Cl, Br, I, or a tetrahaloborate; and $Ar_1$, $Ar_2$, and $Ar_3$ are as defined above, comprising the steps of:
cleaving a triarylmethyl protecting group during the course of oligonucleotide synthesis;
collecting the effluent from the cleavage, the effluent containing free triarylmethyl protecting group;
contacting the free triarylmethyl protecting group with a base to form a triarylmethyl alcohol; and
reacting the triarylmethyl alcohol with
   a) halide reagent to form the triarylmethyl halide protecting reagent; or
   b) a tetrahaloborate reagent to form the triarylmethyl teterahaloborate protecting reagent.

In some preferred embodiments, the triarylmethyl protecting group is cleaved during the course of oligonucleotide synthesis according to the phosphoramidite method.

In the context of the present invention, the term "oligonucleotide" refers to a plurality of joined nucleotide units formed in a specific sequence. The term nucleotide has its accustomed meaning as the phosphoryl ester of a nucleoside. The term "nucleoside" also has its accustomed meaning as a pentofuranosyl sugar which is bound to a nucleosidic base (i.e., a nitrogenous heterocyclic base or "nucleobase").

In another preferred embodiment of the invention the triarylmethyl halide is attached to a resin (polymer). Triarylmethyl halide resins are well known in the art and have been used for the solid-phase immobilization of alcohols, amines, caboxylic acids, phonols, imidazoles and thiols. See, for example, the Calbiochem-Novabiochem Corp. Catalog for Combinatorial Chemistry 1999, at page S16, wherein a detailed reactivity table is provided. Diols and diamines are effectively monoprotected in the process, allowing the other functionality to be further elaborated. The cleavage of amines and alcohols from trityl resins is generally achieved with 1–5% TFA in DCM containing 1–5% triisopropylsilane (TIS). Addition of silanes such as TIS accelerates the cleavage of carboxy, hydroxy, phoenoxy and thiol functions from the trityl resins. The cleavage rates of amino, imino, and amide functions are not appreciably affected by silanes. Substitution of trityl linkers with alkyl, alkoxy or halide functional groups results in substituted trityl linkers with different susceptibilities to acidic cleavage.

A protected nucleoside having free 5'- and 3'-OH groups is typically attached to a commercially available triarylmethyl halide resin by reaction with bound triarylmethyl halide group to give a solid support bound nucleoside. The attachment is preferably made through a free 5'-OH group but may also be made via other functionalities such as for example exocyclic amino functionalities located on heterocyclic bases. The bound nucleoside is further functionalized as per established protocols to form an activated phosphorus intermediate. Such intermediate may be prepared from a plurality of protocols well known in the art such as for example reaction of the free 3'-hydroxyl group with a chloroamidite or bis-amidite reagent to form a phosphoramidite. The resulting activated phosphorus intermediate is reacted with a further protected nucleoside having a free 3'-hydroxyl group to form a dimer that is cleaved from the resin bound triarylmethyl protecting group using acid. The dimer may be utilized as the initial monomeric nucleoside e.g. attachment to a triarylmethyl halide resin and further elongated by a further iteration of the process. The loading and cleavage of resins functionalized with triarylmethyl halides is further illustrated in the literature (See for example The Combinatorial Index by Barry A. Bunin, Academic Press, 1998, pp 52–55, incorporated by reference herein in its entirety)

It is significant that at present, all of the above resins are used once and then discarded. In addition, there are no reported teachings of the recovery and reuse of these expensive resins.

Typically, these resins are employed in a two step procedure. First, a resin is loaded or attached with the starting material. Then the second step involves cleavage of the synthesized product from the insoluble polymeric support as illustrated above for a dimer. Upon cleavage a triarylmethyl cation is generated on the resin and the product is released in to the solution.

In a more general protocol triarylmethyl halide resins are used to prepare a variety of compounds such as oligomeric compounds and combinatorial compounds. The preparation of compounds can be performed on an automated synthesizer or by manual protocols. The starting material is can be, for example, an appropriately protected nucleoside, or an appropriate alcohol, amine, caboxylic acid, phenol, imidazole or thiol dissolved in a suitable solvent. To this solution is optionally added an appropriate amount of base (which base is not required for some compounds such as, for example, amines). This mixture is then added to the resin and allowed to react under conditions of time, temperature and pressure (typically with agitation) effective to form a bond between the selected starting material and the resin bound triarylmethyl group. At the end of loading the resin is filtered and washed with a suitable solvent to remove unreacted materials and reagents. The loading of material can be determined by several standard methods such as IR, UV and NMR.

The insoluble polymer support bearing a triarylmethyl group, which is now attached to a starting material, such as appropriate nucleoside, alcohol, amine, caboxylic acid, phenol, imidazole or thiol can undergo a series of reactions to build the desired molecule. After a desired molecule has been so synthesized, it can be cleaved from the support by, for example, teatment with an acidic ragent. Generally, resins are suspended or stirred in 1–5% TFA containing 5% TIS or dilute solutions of anhydrous HCl in dry dioxane or solution of substituted acetic acid or acetic acid in halogenated solvent. In some cases, toluene has been also used to replace toxic dichloromethane during cleavage step. After appropriate exposure with an acidic solution, the resin is filtered and washed with a suitable solvent to collect the product.

The resin bound triarylmethyl cation is recycled to the resin bound triarylmethyl halide by first treating it with dilute base in an appropriate solvent. A preferred base and solvent combination is aqueous NaOH in MeOH. Base treatment converts the resin bound triarylmethyl cation to a resin bound triarylmethyl alcohol. The resin is then washed free of water, solvent and alkaline residue. The resin is suspended in toluene or other suitable solvent, which can help in swelling of the resin, and acetylchloride (or other halogenating agent) is added under conditions of time, temperature and pressure (typically with agitation) to give the triarylmethyl chloride functionalized resin. The resin is further purified by filtering and washing with an appropriate solvent followed by drying under vacuum. The recycled resin is ready for another iteration of synthesis as illustrated above.

A variety of insoluble polymers with a wide range of substituted triarylmethyl halides are commercially available. For example, 2-chlorotrityl chloride resin, 4-methyltrityl chloride resin, 4-methoxytrityl chloride resin, 4,4'-dimethoxytrityl chloride resin and trityl chloride resin are listed in Calbiochem catalog for an average price of $40–50/ g.

It will be appreciated that the methods of the present invention can be applied to the synthesis of oligonucleotides by a number of different chemical approaches such as phosphoramidite, phosphotriester and phosphonate chemistries and by solution or solid phase reactions, as has been widely reported in the literature. The nucleotide building blocks and therefore the oligonucleotides synthesized using the methods of this invention may have both naturally occurring and non-naturally occurring constituent sugars, internucleoside linkages and/or nucleobases. Non-naturally occurring sugars, internucleoside linkages and nucleobases are typically structurally distinguishable from, yet functionally interchangeable with, naturally occurring sugars (e.g. ribose and deoxyribose), internucleoside linkages (i.e. phosphodiester linkages), and nucleosidic bases (e.g., adenine, guanine, cytosine, thymine). Thus, non-naturally occurring moieties include all such structures which mimic the structure and/or function of naturally occurring moieties, and which aid in the binding of the oligonucleotide analog to a target, or otherwise advantageously contribute to the properties of the synthesized oligonucleotide.

Representative examples of non-naturally occurring sugars include sugars having any of a variety of substituents attached to their any one or more positions on the sugar. These include 2'-substitutions such as, for example, halides, O-alkyl, O-aminoalkyl, O-alkyloxyalkyl, -protected O-aminoalkyl, O-alkylaminoalkyl, O-dialkylaminoalkyl, O-imidazolylalkyl, O-dialkylaminooxyalkyl, O-alkylaminooxyalkyl, and polyethers of the formula (O-alkyl)$_m$, where m is 1 to about 10. Preferred among these polyethers are linear and cyclic polyethylene glycols (PEGs), and (PEG)-containing groups such as crown ethers and those which are disclosed by Ouchi et al., *Drug Design and Discovery*, 1992, 9, 93, Ravasio et al., *J. Org. Chem.*, 1991, 56, 4329, and Delgardo et al., *Critical Reviews in Therapeutic Drug Carrier Systems*, 1992, 9, 249. Further sugar modifications are disclosed in Cook, *Anti-Cancer Drug Design*, 1991, 6, 585, Cook, Medicinal Chemistry Strategies for Antisense Research, in *Antisense Research and Applications*, Crooke et al., CRC Press Inc., Boca Raton, Fla., 1993. O-Fluoro, O-alkyl, O-aminoalkyl, O-imidazolylalkyl, O-alkylaminoalkyl, and O-aminoalkyl 2'-substitutions are described in U.S. patent application Ser. No. 08/398,901, filed Mar. 6, 1995, entitled Oligomeric Compounds having Pyrimidine Nucleotide(s) with 2' and 5 Substitutions, the disclosure of which is hereby incorporated by reference.

Oligonucleotides bearing sugars having O-substitutions on the ribosyl ring are also amenable to the present invention. Representative substitutions for ring O include S, $CH_2$, CHF, and $CF_2$, see, e.g., Sanghvi and Cook in Carbohydrate Modifications in Antisense Research, ACS Symposium Series 580, ACS Publication, Washington, D.C., 1994.

Representative nucleobases that may be present in the building blocks and oligonucleotides used in the methods of this invention include, adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-aza uracil, cytosine and thymine, 5-uracil (pseudo uracil), 4-thiouracil, 8-halo, oxa, amino, thio, thioalkyl, hydroxyl and other 8-substituted adenines and guanines, 5-trifluoromethyl and other 5-substituted uracils and cytosines, and 7-methylguanine. Further naturally and non-naturally occurring nucleobases include those disclosed by Metrigan et al. in U.S. Pat. No. , 3,687,808, by Sanghvi, in Chapter 15, *Antisense Research and Applications*, Ed. S. T. Crooke and B. Lebleu, CRC Press, Boca Raton, Fla., 1993, by Englisch et al., *Angewandte Chemie*, Int. Ed., 1991, 30, 613, in *The Concise Encyclopedia of Polymer Science and Engineering*, Ed. J. I. Kroschwitz, John Wiley and Sons, 1990, pp.858–859, and by Cook, *Anti-Cancer Drug Design*, 1991, 6, 585. The disclosures of each of the foregoing is incorporated by reference in their entirety. The terms 'nucleosidic base' and 'nucleobase' are further intended to include heterocyclic compounds that can serve as nucleosidic bases, including certain 'universal bases' that are not nucleosidic bases in the most classical sense, but function similarly to nucleosidic bases. One representative example of such a universal base is 3-nitropyrrole.

Representative internucleotide linkages that may be present in the oligonucleotides include, but are not limited to, phosphodiester, phosphorothioate, phosphoroselenoate, phosphorodithioate, H-phosphonate, methyl phosphonate, and alkyl phosphonate. These linkages may be between the 5'-O one nucleotide unit and any one of the 2'-, 3'-, or 4'-positions of another nucleotide unit. See generally, Sanghvi in "DNA with Altered Backbones in Antisense Applications" in Comprehensive Organic Natural Product Chemistry, Vol. 7, Elservier Science Ltd., Oxford, 1998, which is hereby incorporated by reference in its entirety.

Additional advantages and novel features of this invention will become apparent to those skilled in the art upon examination of the examples thereof provided below, which should not be construed as limiting the appended claims.

EXAMPLE 1

Figure 2:
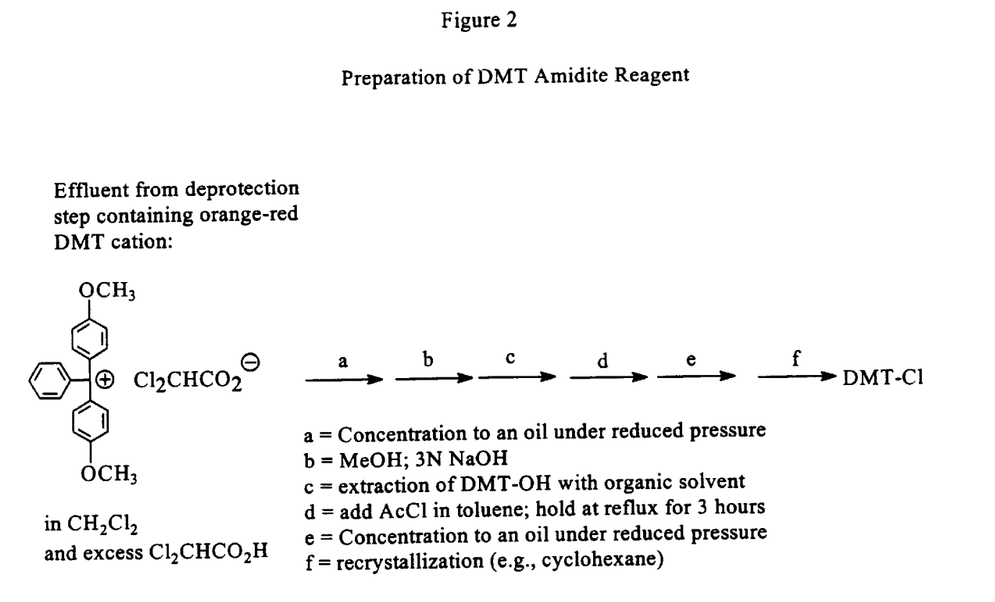
FIG. 2 shows the preparation of amidite DMT reagent according to some preferred embodiments of the invention.

A 60 mmole scale synthesis of oligonucleotide was commenced on a Pharmacia OligoProcess instrument. Deprotection of the 5'-protecting groups during this synthesis was performed using a 3% solution of dichloroacetic acid in dichloromethane. The waste stream generated from the cleavage of the 5'-O-dimethoxytrityl protecting groups during the deblocking cycles (FIG. 1, step I) was collected manually (12 L of 3% DCA in DCM containing trityl cation). The solution was concentrated under vacuum (FIG. 2, step a) to remove most of the dichloromethane. The oily-red residue was then dissolved in MeOH (1.8 L) and NaOH (aqueous, 3 N, 1.5 L) was added over a period of 1 hour followed by stirring for 16 hours ambient temperature (FIG. 2, step b). The reaction mixture was concentrated under vacuum to remove most of the MeOH. The remaining aqueous layer was extracted with toluene (200 mL×3) (FIG. 2, step c) and the organic phases were combined, and dried ($Na_2SO_4$). A small sample (50 mL) of the toluene solution was evaporated to give 4,4'-dimethoxytrityl alcohol (DMT-OH in FIG. 1). The compound was verified by mass spectrometry: MS (FAB) m/z 343 ($MNa^+$).

The toluene solution was then concentrated to a minimum volume (~80 mL). Acetylchloride (8.5 mL, 9.42 g, 0.12 mol) was added and the solution was refluxed for 2 hours under argon (FIG. 1, step d). Reaction mixture was then cooled to room temperature, and the solution was concentrated under vacuum (FIG. 2, step e). Cyclohexane (100 mL) was added to the residue and the mixture was allowed to stand in a refrigerator for 16 hours. The crystallized material filtered, washed with cold cyclohexane (50 mL×2) and dried under reduced vacuum to furnish DMT-Cl (17.5 g, 89.7%). m.p. 122–124° C. [Rathore et al., Indian J. Chem. 34B (1995) 634–635: 119–123° C.] $^1$H NMR (200 MHZ, $CDCl_3$) d 3.84 (s, 6H), 6.87 (d, 4H), 7.20–7.36 (m, 9H). $^{13}$C NMR (50 MHZ, $CDCl_3$) d 55.37, 82.15, 113.02, 127.76, 129.76, 131.09, 137.85, 145.84, 159.09. Anal. Calcd. for $C_{21}H_{19}ClO_2$ (338.83): C, 74.44; H, 5.65. Found: C, 74.66; H, 5.82. The identity of recaptured DMT-Cl was further confirmed by TLC cospotting with an authentic sample in three different solvents ($CH_2Cl_2$: $R_f$ 0.25; $CH_3CN$: $R_f$ 0.9; 30% EtOAc in Hexanes: $R_f$ 0.4). In addition, this DMT-Cl was also used for the preparation of 5'-O-DMT protected nucleosides and the m.p., $^1$H and $^{13}$C NMR, and C, H, and N analyses were identical to literature values for the given compounds.

EXAMPLE 2

A 60 mmole scale synthesis of oligonucleotide is commenced as in Example 1. Deprotection of the 5'-protecting groups during this synthesis is performed using a 3% solution of dichloroacetic acid in dichloromethane. The waste stream generated from the cleavage of the 5'-O-dimethoxytrityl protecting groups during the deblocking cycles is collected manually (12 L of 3% DCA in DCM containing trityl cation). The solution is concentrated under vacuum to remove most of the dichloromethane. The oily-red residue is then dissolved in MeOH (1.8 L) and NaOH (aqueous, 3 N, 1.5 L) is added over a period of 1 hour followed by stirring for 16 hours ambient temperature. The reaction mixture is concentrated under vacuum to remove most of the MeOH. The remaining aqueous layer is extracted with toluene (200 mL×3) (FIG. 2, step c) and the organic phases are combined, and dried ($Na_2SO_4$). The toluene solution is then concentrated to a minimum volume (~80 mL).

The 4,4'-dimethoxytrityl alcohol is then converted to the 4,4'-dimethoxytrityl tetrafloroborate according to the procedure of Bleasdale, C. et al., J. Chem. Soc. Perkin Trans. 1:803–805 (1990). The 4,4'-dimethoxytrityl alcohol is dissolved in 20 molar equivalents of warm acetic anhydride. The solution is allowed to cool, and 40% auqeous tetrafluoroboric acid (4–5 molar equivalents) is added at a rate sufficient to ensure that the temperature does not rise above 25° C., forming a dark red solution. Addition of ether to the solution yields the product as deep orange crystals.

EXAMPLE 3

Synthesis of TA Dimer Using Resin Bound 4,4'-dimethoxytrityl Chloride

A 4-methoxytrityl chloride resin (1 mmol), (Calbiochem-Novabiochem Corp., Combinatorial Chemistry Catalog, March 99), triethylamine (2 mmol) and thymidine (1 mmol) are shaken in dry pyridine (5 mL) at room temperature under an argon atmosphere. The progress of the reaction is monitored by tlc for the disappearance of thymidine from solution. The support is washed with dichloromethane (3×25 mL) and dried to provide the protected thymidine attached to resin. The resin is resuspended in anhydrous acetonitrile (10 mL) and phosphitylated with 2-cyanoethyl-N,N,N'N'-tetraisopropyl phosphoradiamidte (1.1 mmol) in presence of pyridinium trifluoroacetate (1.1 mmol) following a standard protocol ((prepared as per the disclosure of U.S. patent application Ser. No. 09/177,953, filed Jun. 2, 1998, entitled "Activators for Oligonucleotide Synthesis", also identified by attorney docket ISIS-3148, commonly assigned with this application, the disclosure of which is herein incorporated by reference). Upon completion of the phosphitylation, the support is washed with acetonitrile (3×25 mL) to remove excess reagents. The resin bound phosphoramidite is resuspended in acetonitrile (10 mL) and reacted with 6-N-benzoyl-2'-deoxy-3'-O-levulinoyladenosine (1.1 mmol, prepared according to method described in the literature (Perkin, J. Chem. Soc., 1999, 1, 1477) in the presence of 1-H-tetrazole (2 mmol) following a standard literature protocol (Oligonucleotide Synthesis by R. P. Iyer and S. Beaucage in Comprehensive Natural Products Chemistry Vol.7, Vol. Ed. E. T. Kool, Elsevier 1999, page 105–152). After coupling the support is washed with acetonitrile (3×25 mL) and the phosphite is oxidized with phenylacetyl disulfide/3-picoline in acetonitrile (described in WO 98/39290, published Sep. 11, 1998). The TA dimer is then cleaved from the support following an acid treatment as previously illustrated in the examples above.

After the cleavage of the TA dimer the resin bound trityl cation is regenerated. The resin bound triarylmethyl cation is recycled to the resin bound triarylmethyl halide by first treating it with dilute base in an appropriate solvent. A preferred base and solvent combination is aqueous NaOH in MeOH. Base treatment converts the resin bound triarylmethyl cation to a resin bound triarylmethyl alcohol. The resin is then washed free of water, solvent and alkaline residue. The resin is suspended in toluene or other suitable solvent, which can help in swelling of the resin, and acetylchloride (or other halogenating agent) is added under conditions of agitation, time, temperature and pressure to give the triarylmethyl chloride functionalized resin. The resin is further purified by filtering and washing with an appropriate solvent followed by drying under vacuum. The recycled resin is ready for another iteration of synthesis using a monomeric or oligomeric nucleoside as illustrated above for the monomer.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the present invention, and that such changes and modifications may be made without departing from the spirit of the invention. It is, therefore, intended that the appended claims cover all such equivalent variations as fall within the true spirit and scope of the invention.

What is claimed is:

1. A synthetic method comprising:
   providing a compound having an alcohol, amine, caboxylic acid, phenol, imidazole or thiol functionality, the alcohol, amine, caboxylic acid, phenol, imidazole or thiol functionality being protected with a solid support bound triarylmethyl protecting group;
   treating the compound with a deprotecting reagent to produce a solid support bound triarylmethyl cation;
   contacting the solid support bound triarylmethyl cation with a base to form a solid support bound triarylmethyl alcohol; and
   reacting the solid support bound triarylmethyl alcohol with a halide reagent to form a triarylmethyl halide protecting reagent.

2. The method of claim 1 wherein the triarylmethyl halide protecting reagent has the Formula:

wherein:
   X is Cl, Br or I;
   SS is a solid support which can include an optional linking moiety; and
   each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, and pyrenyl; or $Ar_1$, is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, or pyrenyl; or $Ar_2$ and $Ar_3$ together form xanthanen-9-yl or thioxanthen-9-yl.

3. The method of claim 2, wherein the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris(levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl.

4. The method of claim 3, wherein the triarylmethyl protecting group is 4,4'-dimethoxytrityl.

5. The method of claim 1 wherein the base is sodium hydroxide, potassium hydroxide, lithium hydroxide or barium hydroxide.

6. The method of claim 5, wherein the base is sodium hydroxide.

7. The method of claim 1 wherein the halide reagent is acetyl chloride, acetyl bromide, acetyl iodide, thionyl chloride, thionyl bromide, phosphorus trichloride, phosphorus tribromide, phosphorus oxychloride, or carbon tetrabromide.

8. The method of claim 7, wherein the halide reagent is acetyl chloride.

9. The method of claim 1, wherein the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris(levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl;
   the base is sodium hydroxide, potassium hydroxide, lithium hydroxide or barium hydroxide; and
   the halide reagent is acetyl chloride, acetyl bromide, acetyl iodide, thionyl chloride, thionyl bromide, phosphorus trichloride, phosphorus tribromide, phosphorus oxychloride, or carbon tetrabromide.

10. The method of claim 9 wherein the triarylmethyl protecting group is 4,4'-dimethoxytrityl.

11. The method of claim 9 wherein the base is sodium hydroxide.

12. The method of claim 9 wherein the halide reagent is acetyl chloride.

13. The method of claim 1 wherein the triarylmethyl protecting group is 4,4'-dimethoxytrityl; the base is sodium hydroxide; and the halide reagent is acetyl chloride.

14. The method of claim 1 wherein the contacting the solid support bound triarylmethyl cation with a base is performed in a water-miscible organic solvent.

15. The method of claim 14 wherein the solvent is methanol, ethanol, propanol, acetonitrile, or tetrahydrofuran.

16. The method of claim 1 wherein the solid support bound triarylmethyl alcohol is contacted with the halide reagent in a water-immiscible solvent.

17. The method of claim 16 wherein the water-immiscible solvent is diethyl ether, diisopropyl ether, ethyl acetate, dichloromethane, chloroform, or toluene.

18. The method of claim 2 wherein said solid support is controlled pore glass, oxalyl-controlled pore glass, aminopolyethyleneglycol (TENTAGEL), polystyrene or a derivatized polystyrene.

19. The method of claim 1 where said derivatized polystyrene is copoly(styrene 1% divinylbenzene).

* * * * *